United States Patent

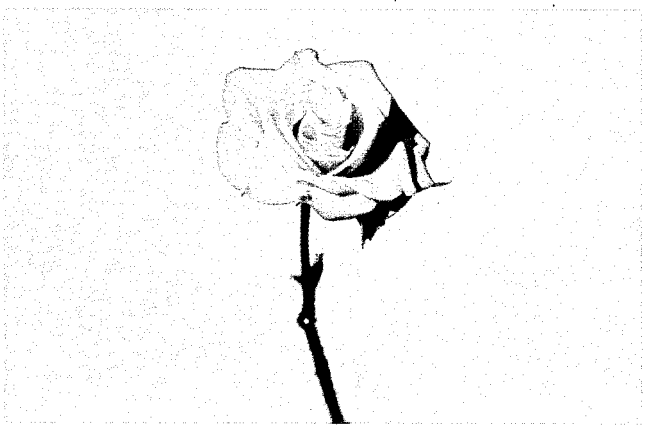
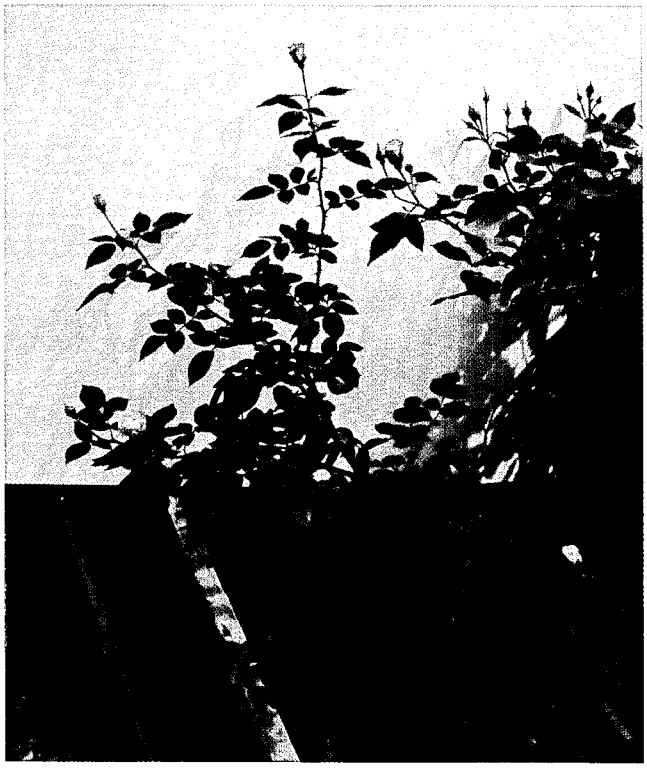

Plant Pat. 3,840

Patented Mar. 9, 1976

3,840

ROSE PLANT (CHIBI)

George Y. Umeda and Daniel S. Shinoda, San Leandro, Calif., assignors to San Leandro Nursery Co., San Leandro, Calif.

Filed Feb. 6, 1975, Ser. No. 547,575

Int. Cl. A01h *5/00*

U.S. Cl. Plt.—28 1 Claim

ABSTRACT OF THE DISCLOSURE

A new variety of rose plant distinguished by its continuous production of mandarin red blooms and an exceptionally long lasting quality as cut flowers, the plant being much branched and having a vigorous growth habit with the flowers being slightly smaller in size than the usual commercial floribunda such as Junior Bridesmaid (Plant Pat. 2,446).

BACKGROUND OF THE NEW PLANT

This new variety of rose plant originated as a seedling from a cross of Junior Bridesmaid (P.P. 2,446) and Rumba (P.P. 1,919) made by us during breeding efforts carried on by us at San Lorenzo Nursery, at San Leandro, Calif., since 1972 in its greenhouses with the object of producing commercial cut flowers for the market. The plant was discovered by us in 1972 and because it appeared to possess the most desirable characteristics of its parents, as well as profuse production of well formed blossoms of unusual color, this plant was selected for propagation and testing. Asexual reproduction of this plant by cuttings and potting in a propagating house in a greenhouse bed, carried on by us at San Leandro, Calif., since 1972, demonstrated that the desirable characteristics were well fixed, and propagation through successive generations by budding has shown the novel features to hold true from generation to generation.

DESCRIPTION OF THE DRAWING

Our new variety of rose plant is illustrated by the accompanying full color photographic drawing, in which:

FIG. 1 is a full face view of one of the blossoms on a stem, and

FIG. 2 is a full view of several plants in a bed in a greenhouse, the colors shown being as nearly true as is possible to obtain by conventional photographic procedures.

DESCRIPTION OF THE NEW PLANT

The following is a detailed description of the garden rose plant with specifications of color according to Robert S. Wilson's Horticultural Colour Chart as issued by the British Colour Council and the Royal Horticultural Society.

*The plant*

Origin:—Seedling.
Parentage:
Seed parent—Junior Bridesmaid, P.P. 2,446.
Pollen parent—Rumba, P.P. 1,919.
Classification:
Botanic—Rosa hybrid.
Commerical—Floribunda.
Form: Bush.
Height: To at least 3 feet.
Growth: Vigorous and much branched.
Habit: Tall, bushy and much branched.
Foliage: Quantity—Abundant.
Leaves: Shape—Elongate ovate with apex pointed, margin serrated. Size: 3 inches by approximately 1½ inches at widest point. Texture: Smooth.

Color: Upper side—Medium Green, RHS 139A, Lower side—Grey-Green, RHS 147B.
Leaflets: Five in number. Size: About 1¼ inches long. Petioles: Length—¼ inch. Ribs and veins: Yes. Shape: Ovate with serrated margins. Texture: Smooth. Color: Substantially the same as ful grown leaf. Thorns: Yes at ⅛" long; color—Rose.

*The bud*

Shape: Cupped.
Size: Medium, about ½ inch in diameter with a depth of ¼ inch.
Opening Rate: Slow.
Sepals: Branched and stand up, and narrow pointed.
Color: Inside—Light Green, RHS 193B. Outside—Pistachio Green, RHS 139C.
Calyx: Pear shaped.
Size: About ¾ inch wide and 1 inch long.
Aspect: Smooth.
Peduncle: Legth 1 inch, hairy and erect.
Color: Light Green, RHS 143C.

*The flower*

Blooming Habit: Spring and fall—profusely.
Size: Small—1½ inches in diameter and ¼ inch in depth.
Borne: Singly and in clusters.
Shape: When bloom first opens it is cup shaped and does not change form later.
Petalage: Blossom has 19 to 23 petals in regular imbricated arrangement.
Color: Outer Petals—Mandarin Red, RHS 40B; Base, Yellow, RHS 4D. Inside petals—Mandarin Red, RHS 40B; base, Yellow, RHS 4D. Reverse side—Claret Rose, RHS 50B.
Texture: Leathery.
Appearance: Satiny.
Petaloids: Two in number.
Size: ¼ inch.
Color: Vermilion, RHS 41B.
Peduncle: Length—About 1 inch, sturdy and upright.
Color: Green, RHS 143C.
Discoloration: No, after full bloom.
Effect of Weather: Not affected by wet or hot weather.
Persistence: Petals stay on stem about two weeks.
Disease Resistance: Resistant to powdery mildew.
Fragrance: Slight.
Lasting Quality: On plant—2 weeks. As cut flower—10 days.

*Reproductive organs*

Stamens:
Anthers: About 55, regularly arranged and about ⅛ inch long.
Filaments: About ⅛ inch long. Color: Generally white.
Pollen: Color—Primrose Yellow, RHS 4D.
Pistils: About 40 in number.
Styles: 1/16 inch in length.
Stigmas: Color—Primrose Yellow, RHS 4C.
Characteristics of Ovaries: Color—Willow Green, RHS 149D.

*Fruit*

Fertile: Yes.
Shape: Pear shaped.
Color at Maturity: Brownish Yellow, RHS 163A.

This variety of rose plant is a vigorous grower, hardy and resistant to powdery mildew, as observed at San Leandro, Calif., where such diseases are ordinarily apt to be found. Its blossom color is outstanding and distinctly different than either of its parent varieties and, with the advantageous plant habit, this new plant is outstanding as a cut commercial rose.

We claim:

1. A new and distinct variety of rose plant, substantially as herein shown and described, characterized by the mandarin red coloring of its small, high centered blossoms which are produced continuously from the spring to the fall and profusely on vigorous, upright, and much branched plants which reach a height of three feet, the cut flowers having long lasting quality.

No references cited.

ROBERT E. BAGWILL, Primary Examiner